United States Patent [19]
Wilding et al.

[11] Patent Number: 5,486,335
[45] Date of Patent: *Jan. 23, 1996

[54] ANALYSIS BASED ON FLOW RESTRICTION

[75] Inventors: Peter Wilding, Paoli; Larry J. Kricka, Berwyn, both of Pa.

[73] Assignee: Trustees of the University of Pennsylvania, Philadelphia, Pa.

[*] Notice: The term of this patent shall not extend beyond the expiration date of Pat. No. 5,296,375.

[21] Appl. No.: 427,493

[22] Filed: Apr. 24, 1995

Related U.S. Application Data

[63] Continuation of Ser. No. 250,100, May 26, 1994, abandoned, which is a continuation of Ser. No. 877,701, May 1, 1992, abandoned.

[51] Int. Cl.$^6$ ............................................. G01N 21/00
[52] U.S. Cl. ..................... 422/55; 422/58; 422/61; 422/68.1; 422/73; 435/7.2; 435/7.21; 435/287.2; 435/288.7; 435/287.1; 436/164; 436/524; 436/809
[58] Field of Search ...................... 422/55, 58, 61, 422/68.1, 73; 435/2, 7.2, 7.21, 6, 291; 436/164, 180, 501, 524, 809; 356/246

[56] References Cited

U.S. PATENT DOCUMENTS

| | | | |
|---|---|---|---|
| 3,799,742 | 3/1974 | Coleman | 422/61 |
| 4,233,029 | 11/1980 | Columbus | 422/100 |
| 4,302,313 | 11/1981 | Columbus | 204/195 R |
| 4,618,476 | 10/1986 | Columbus | 422/100 |
| 4,676,274 | 6/1987 | Brown | 422/82 |
| 4,790,640 | 12/1988 | Nason | 350/534 |
| 4,886,761 | 12/1989 | Gustafson et al. | 436/518 |
| 4,906,439 | 3/1990 | Grenner | 422/55 |
| 4,908,112 | 3/1990 | Pace | 356/344 |
| 4,911,782 | 3/1990 | Brown | 156/633 |
| 4,963,498 | 10/1990 | Hillman et al. | 436/69 |
| 5,135,720 | 8/1992 | Uchida | 422/69 |
| 5,147,606 | 9/1992 | Charlton et al. | 422/56 |

FOREIGN PATENT DOCUMENTS

| | | |
|---|---|---|
| 0320308 | 6/1989 | European Pat. Off. . |
| 0430248 | 6/1991 | European Pat. Off. . |
| 0439182 | 7/1991 | European Pat. Off. . |
| 0483117 | 4/1992 | European Pat. Off. . |

(List continued on next page.)

OTHER PUBLICATIONS

Kinosita, Jr. et al; "Dual-view microscopy with a single camera ..." entire document. J. Cell. Biol. vol. 115, (1) Oct. 1991, pp. 67–73.

(List continued on next page.)

Primary Examiner—Robert J. Warden
Assistant Examiner—Hien Tran
Attorney, Agent, or Firm—Dann, Dorfman, Herrell and Skillman

[57] ABSTRACT

Disclosed are devices and methods for detecting the presence of a preselected analyte in a fluid sample. The invention provides a device comprising a solid substrate, typically on the order of a few millimeters thick and approximately a 0.2 to 2.0 centimeters square, microfabricated to define a sample inlet port and a mesoscale flow system. A sample is passed through the mesoscale flow system, and the restriction or blockage of flow through the flow system is detected as a positive indication of the presence of the analyte. The mesoscale flow system includes in one embodiment a primary sample flow channel extending from the inlet port, and a fractal region, in fluid communication with the flow channel, comprising bifurcations leading to plural secondary flow channels. The device may be adapted for operation in conjunction with a pump, for example, to induce flow of a sample through the flow system. A detector may also be provided for detecting analyte induced changes in flow properties in the mesoscale flow system. The devices of the invention may be used in a wide range of applications, including the detection of cells or macromolecules, such as viruses.

47 Claims, 9 Drawing Sheets

FOREIGN PATENT DOCUMENTS

| | | |
|---|---|---|
| 3915920 | 11/1990 | Germany . |
| 2191110 | 12/1987 | United Kingdom . |
| 90/09596 | 8/1990 | WIPO . |
| WO91/13338 | 9/1991 | WIPO . |
| 91/15750 | 10/1991 | WIPO . |
| 91/16966 | 11/1991 | WIPO . |

OTHER PUBLICATIONS

Pfahler, et al., "Liquid Transport in Micron and Submicron Channels," *Sensors and Actuators A*, 21–23:431–434 (1990).

Tracey, et al., "Microfabricated Microhaemorheometer," *IEEE International Conference on Solid–State Sensors and Actuators*, pp. 82–84 (1991).

Washizu, et al., "Handling of Biological Cells Using Fluid Integrated Circuit," *IEEE Industry Applications Society Annual Meeting*, 2:1735–1740 (1988).

Kinosita et al., "Dual–View Microscopy With A Single Camera: Real–Time Imaging Of Molecular Orientations And Calcium," *J. Cell Biol*, 115:67–73 (1991) (Abstract).

Anderson, *Nature*, 355:379 (1992).

Angell, et al., *Scientific American*, 248:44–55 (1983).

Appenzeller, *Science*, 254:1300–1342 (1991).

Barany, *Proc. Natl. Acad. Sci*, 88:189–192 (1991).

Brown, "Development of a Stopped–Flow Cytometer," NSF Grant No. ISI 87–60730.

Brunette, *Exper. Cell Res.*, 167: 203–217 (1986).

Brunette, *Exper. Cell Res.*, 164: 11–26 (1986).

Columbus et al., *Clin. Chem.*, 33:1531–1537 (1987).

DeLuca et al., *Arch. Biochem. Biophys.*, 255:285–292 (1983).

Dessy, *Chemometrics and Intelligent Laboratory Systems*, 8:311 (1990), Abstract.

Esashi et al., "Integrated Flow Control Systems Fabricated on a Silicon Wafer," Proceedings, Electrochemical Society Conference, HI (18–23 Oct., 1987), Electrochemical Society, Pennington, NJ, pp. 31–38B, 1987.

Fromherz et al., *Biochimica et Biophysica Acta*, 1062:103–107 (1991).

Goin et al., *Clin. Chem.*, 32:1655–1659 (1986).

Haller in: *Solid Phase Biochemistry*, W. H. Scouten, Ed., John Wiley, New York, pp. 535–597 (1983).

Hanazato et al., *IEEE Transactions Electron. Devices;* ED33:47–51 (1986).

Hoopman, "Microchanneled Structures," Applied Technology Laboratory, 3M Center, St. Paul, MN 55144–1000.

Howe et al., *IEEE Transactions Electron Devices*, ED33:499–506 (1986).

Hung et al, *Med. & Biol. Engng.*, 9:237–245 (1971).

Jonsson, *Methods in Enzymology*, 137:381–389 (1988).

Kennedy et al., *Clin. Chem. Acta*, 70:1–31 (1976).

Kenny et al., *Appl. Phys. Lett.*, 58:100–102 (1991).

Kikuchi et al., "Microchannels Made on Silicon Wafer for Measurement of Flow Properties of Blood Cells," *Biorheology, 26:1055 (1989), Abstract.*

Kittilsland et al., *Journal de Physique*, 49 (C4):641–644 (1988).

Kittilsland et al., *Sensors and Activators*, A21–A23:904–907 (1990).

Kricka et al., "Liquid Transport in Micron and Submicron Channels," SPIE, 1167:159–168 (1989).

Kricka et al., *Clin Chem.*, 26:741–744 (1980).

LaCelle, *Blood Cells*, 12:179–189 (1986).

Mandenius et al., *Anal. Biochem.*, 137:106–114 (1984).

Mandenius et al., *Anal. Biochem.*, 170:68–72 (1988).

Mandenius et al., *Methods in Enzymology*, 137:388–394 (1988).

Manz et al., *Trends in Anal. Chem.*, 10:144–149 (1991).

Masuda et al. *Proc. IEEE/IAS Meeting*, pp. 1549–1553 (1987).

McCartney et al., *Cancer Res.*, 41:3046–3051 (1981).

Moghissi et al., *Am. J. Obstet. Gynecol.*, 114:405–(1972).

Nakamura, *Immunochemical Assays and Biosensor Technology for the 1990's*, American Society of Microbiology, Washington, D.C., pp. 205–215 (1992).

Nakamura et al., *Anal. Chem.*, 63:268–272 (1991).

Parce et al., *Science*, 24:243–247 (1989).

Rosenberg et al., *Clin. Chem.*, 30:1462–1466 (1984).

Rosenberg et al,. *Clin. Chem.*, 31:1444–1448 (1985).

Sankolli et al., *J. Imun. Methods*, 104:191–194 (1987).

Sato, et al., *Sensors and Actuators*, A21–A23:948–951 (1990).

Shoji, et al., *Sensors and Actuators*, 15:101–107 (1988).

Stange et al., *Biomaterials*, 9:3–6 (1988).

Van Lintel, *Sensors and Actuators*, 15:153–167 (1988).

Wallis et al., *J. Amer. Ceramic Soc.*, 53;563–567 (1970).

Washizu et al., *Proceedings IEEE/IAS Meeting*, pp. 1735–1740 (1988).

Weissman et al., *Am. Inst. Chem. Eng. J.*, 17:25–30 (1971).

Zemel et al., in: *Fundamentals and Applications of Chemical Sensors*, D. Schuetzle and R. Hammerle, Eds., Washington, D.C., 1986, p. 2.

Biotrack, Ciba Corning, May, 1989.

Wilding, *Advanced Hospital Technology Laboratory*, Oct., 1990 pp. 38–42.

Roche, On–Trak™, Sep., 1988.

ANALYSIS BASED ON FLOW RESTRICTION

This is a continuation of application Ser. No. 08/250,100, filed May 26, 1994, now abandoned, which is a continuation of application Ser. No. 07/877,701, filed May 1, 1992.

REFERENCE TO RELATED APPLICATIONS

This application is being filed contemporaneously with the following related applications: U.S. Ser. No. 07/877,702, filed May 1, 1992, Mesoscale Detection Structures; U.S. Ser. No. 07/877,536, filed May 1, 1992, now U.S. Pat. No. 5,304,487, Fluid Handling in Mesoscale Analytical Devices; U.S. Ser. No. 07/877,667, filed May 1, 1992, Mesoscale Polynucleotide Amplification Analysis; and U.S. Ser. No. 07/877,661, filed May 1, 1992, now U.S. Pat. No. 5,296,375, Mesoscale Sperm Handling Devices, the disclosures of which are incorporated herein by reference.

BACKGROUND OF THE INVENTION

This invention relates generally to methods and apparatus for conducting analyses. More particularly, the invention relates to the design and construction of small, typically single-use, modules capable of rapidly determining the presence of an analyte in a fluid sample.

In recent decades the art has developed a very large number of protocols, test kits, and cartridges for conducting analyses on biological samples for various diagnostic and monitoring purposes. Immunoassays, agglutination assays, and analyses based on polymerase chain reaction, various ligand-receptor interactions, and differential migration of species in a complex sample all have been used to determine the presence or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101–107 (1988). Sato et al. reported a cell fusion technique using micromechanical silicon devices. Sato et al., *Sensors and Actuators*, A21–A23:948–953 (1990). Ciba Corning Diagnostics Corp. (USA) has manufactured a microprocessor-controlled laser photometer for detecting blood clotting.

Micromachining technology originated in the microelectronics industry. Angell et al., *Scientific American*, 248:44–55 (1983). Micromachining technology has enabled the manufacture of microengineered devices having structural elements with minimal dimensions ranging from tens of microns (the dimensions of biological cells) to nanometers (the dimensions of some biological macromolecules). This scale is referred to herein as "mesoscale". Most experiments involving mesoscale structures have involved studies of micromechanics, i.e., mechanical motion and flow properties. The potential capability of mesoscale structures has not been exploited fully in the life sciences.

Brunette (*Exper. Cell Res.*, 167:203–217 (1986) and 164:11–26 (1986)) studied the behavior of fibroblasts and epithelial cells in grooves in silicon, titanium-coated polymers and the like. McCartney et al. (*Cancer Res.*, 41:3046–3051 (1981)) examined the behavior of tumor cells in grooved plastic substrates. LaCelle (*Blood Cells*, 12:179–189 (1986)) studied leukocyte and erythrocyte flow in microcapillaries to gain insight into microcirculation. Hung and Weissman reported a study of fluid dynamics in micromachined channels, but did not produce data associated with an analytic device. Hung et al., *Med. and Biol. Engineering*, 9:237–245 (1971); and Weissman et al., *Am. Inst. Chem. Eng. J.*, 17:25–30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.*, 33:1531–1537 (1987). Masuda et al. and Washizu et al. have reported the use of a fluid flow chamber for the manipulation of cells (e.g. cell fusion). Masuda et al., *Proceedings IEEE/IAS Meeting*, pp. 1549–1553 (1987); and Washizu et al., *Proceedings IEEE/IAS Meeting* pp. 1735–1740 (1988). The art has not fully explored the potential of using mesoscale devices for the analyses of biological fluids and detection of microorganisms.

The current analytical techniques utilized for the detection of microorganisms are rarely automated, usually require incubation in a suitable medium to increase the number of organisms, and invariably employ visual and/or chemical methods to identify the strain or sub-species. The inherent delay in such methods frequently necessitates medical intervention prior to definitive identification of the nature of an infection. In industrial, public health or clinical environments, such delays may have serious consequences. There is a need for convenient systems for the rapid detection of microorganisms.

An object of the invention is to provide analytical systems that can analyze microvolumes of sample and produce analytical results rapidly. Another object is to provide easily mass produced, disposable, small (e.g., less than 1 cc in volume) devices having mesoscale functional elements capable of rapid, automated analyses of preselected molecular or cellular analytes, in a range of applications. It is a further object of the invention to provide a family of such devices that individually can be used to implement a range of rapid tests, e.g., tests for bacterial or viral infection, sperm motility, blood parameters, contaminants in food, water, or body fluids, and the like. Yet another object is to provide a family of analytical assay protocols for detecting the presence of an analyte wherein the information indicative of a positive assay is obtained by measuring directly or indirectly alteration of flow properties of fluid flowing through a restricted passage.

SUMMARY OF THE INVENTION

The invention provides methods and apparatus for detecting the presence of an analyte in a fluid sample. In one embodiment, the invention provides a device comprising a solid substrate, typically on the order of a few millimeters thick and approximately a 0.2 to 2.0 centimeters square, microfabricated to define a sample inlet port and a mesoscale flow system. The invention provides a method wherein a sample fluid is passed through the mesoscale flow system, and the analyte induced restriction or blockage of flow through the system is detected as a positive indication of the presence of the analyte. In one embodiment, the mesoscale flow system includes a primary sample flow channel, extending from the inlet port, and a fractal region, in fluid communication with the primary flow channel, comprising bifurcations leading to plural secondary flow channels. The term "mesoscale" is used herein to define flow passages having cross-sectional dimensions on the order of approximately 0.1 µm to 500 µm, with preferred widths on the order of 2.0 to 500 µm, more preferably 3–100 µm. For many applications, channels of 5–50 µm widths will be useful.

Chambers in the substrates often may have larger dimensions, e.g., widths and lengths of 1–5 mm. Preferred depths are on the order of 0.1 to 100 μm, typically 2–50 μm.

The fractal region typically further comprises junctions, in fluid communication with the secondary flow channels, leading to a third flow channel. The fractal region may comprise equal numbers of bifurcations and junctions disposed serially along the direction of flow. Preferably, but not necessarily, the branching channels in the fractal region progressively decrease in cross-sectional area at each bifurcation and increase at each junction. The fractal flow region is very sensitive to the flow properties of a sample. Means may be provided in the device for inducing flow of the sample through the flow system. Means also may be provided in the device for detecting changes in flow properties, such as restriction or blockage of flow, induced by the presence of an analyte. The devices and methods of the invention may be used to implement a variety of automated, sensitive and rapid tests including analyses for the presence of particular types of cells or macromolecules, for monitoring reactions or cell growth, or for conducting sperm motility testing.

Generally, as disclosed herein, the solid substrate comprises a chip containing the mesoscale flow system. The mesoscale flow system may be designed and fabricated from silicon and other solid substrates using established micromachining methods. The mesoscale flow systems in the devices may be constructed by microfabricating flow channels and one or more fractal regions into the surface of the substrate, and then adhering a cover, e.g., a transparent glass cover, over the surface. The devices typically are designed on a scale suitable to analyze microvolumes (<5 μL) of sample, introduced into the flow system through an inlet port defined, e.g., by a hole communicating with the flow system through the substrate or the cover. Analytes present in very low concentrations (e.g., nanogram quantities) can be rapidly detected (<10 minutes). After an assay is complete, the devices can be discarded.

In one embodiment, a specific binding moiety may be provided in the mesoscale flow system, e.g., in the fractal region, to enhance restriction or blockage of sample flow through the flow system. The binding moieties may comprise particles which bind with a component of the sample to induce detectable particle agglomeration. Optionally, the binding moiety may be immobilized on the internal surfaces of the mesoscale flow system, so that binding induces stenosis of the passage.

The chips typically will be used with an appliance which contains a nesting site for holding the chip, and which mates one or more input ports on the chip with one or more flow lines in the appliance. After a fluid sample, e.g., a biological fluid sample, suspected to contain a particular analyte, such as a cellular contaminant, or toxin, is applied to the inlet port of the substrate, the chip is placed in the appliance and a pump, e.g., in the appliance, is actuated to force the sample through the flow system. Alternatively, a sample may be injected into the chip by the appliance. The sample also may enter the flow system simply by capillary action through an inlet port.

The presence of a preselected analyte in a fluid sample may be detected by sensing analyte-induced changes in sample fluid flow properties, such as changes in the pressure or electrical conductivity, at different points in the flow system. In one embodiment, analyte induced restriction or blockage of flow in the mesoscale flow system, e.g., in the fractal region, may be detected by pressure detectors, e.g., in the appliance used in combination with the device. In another embodiment, analyte-induced changes in conductivity in a region of the flow system caused by introduction of a sample fluid may be readily detected through electrical conductivity sensors in contact with the flow system. For example, the presence of analyte may cause clogging of a restricted flow passage, and beyond the passage, the absence of liquid can be detected by measuring conductivity. The appliance also may include electrical contacts in the nesting region which mate with contacts integrated into the structure of the chip to, e.g., receive electrical signals indicative of a pressure reading, conductivity, or the like, sensed in some region of the flow system to indicate flow restriction, as a positive indication of the presence of the analyte.

Analyte induced changes in flow properties of a sample fluid also may be detected optically, e.g., through a transparent or translucent window, such as a transparent cover over the flow system, or through a translucent section of the substrate itself. The appliance may include sensing equipment, such as a spectrophotometer, capable of detecting analyte induced changes in flow properties of a sample through an optical window in a chip.

The devices of the invention can be adapted to perform a wide range of biological tests. Some of the features and benefits of the devices are summarized in Table 1. A device may include two or more separated flow systems, e.g., fed by a common inlet port, each with different binding moieties in, e.g., different fractal detection regions, to enable the detection of two or more analytes simultaneously. The device may also comprise a control flow system so that data from the sample region and the control region may be detected and compared. The devices can provide rapid clinical tests for the detection of, e.g., pathogenic bacteria, or viruses, or to test, e.g., the motility of a sperm sample. The invention provides methods and devices for use in a wide range of possible assays. Assays may be completed rapidly, and at the conclusion of the assay the chip can be discarded, which advantageously prevents contamination between samples, entombs potentially biologically hazardous material, and provides an inexpensive, microsample analysis.

TABLE 1

| Feature | Benefit |
| --- | --- |
| Flexibility | No limits to the number of chip designs or applications available. |
| Reproducible | Allows reliable, standardized, mass production of chips. |
| Low Cost | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Chips can be sterilized for use in microbiological assays and other procedures requiring clean environments. |
| Sealed System | Minimizes biohazards. Ensures process integrity. |
| Multiple Circuit Capabilities | Can perform multiple processes or analyses on a single chip. Allows panel assays. |
| Multiple | Expands capabilities for assay and |

TABLE 1-continued

| Feature | Benefit |
| --- | --- |
| Detector Capabilities | process monitoring to virtually any system. Allows broad range of applications. |
| Reuseable Chips | Reduces per process cost to the user for certain applications. |

BRIEF DESCRIPTION OF THE DRAWINGS

Like reference characters in the respective drawn figures indicate corresponding parts.

DETAILED DESCRIPTION

The invention provides methods and apparatus for detecting the presence of an analyte in a fluid sample. In one embodiment, the invention provides a device comprising a solid substrate, typically on the order of a few millimeters thick and 0.2 to 2.0 centimeters square, microfabricated to define a sample inlet port and a mesoscale flow system. A sample fluid is passed through the mesoscale flow system, and the analyte induced restriction or blockage of flow through the system is detected as a positive indication of the presence of the analyte.

Analytical devices having mesoscale flow channels and fractal regions can be designed and fabricated in large quantities from a solid substrate material. They can be sterilized easily. Silicon is a preferred substrate material because of the well-developed technology permitting its precise and efficient fabrication, but other materials may be used including polymers such as polytetrafluoroethylenes. The sample inlet and other ports, the mesoscale flow system, including the sample flow channel(s), the fractal region(s), and other functional elements, may be fabricated inexpensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. (See, e.g., Manz et al., *Trends in Analytical Chemistry*, 10: 144–149 (1991)).

Flow channels of varying widths and depths can be fabricated with mesoscale dimensions. The silicon substrate containing a fabricated mesoscale flow channel may be covered and sealed with a thin anodically bonded glass cover. Other clear or opaque cover materials may be used. Alternatively, two silicon substrates can be sandwiched, or a silicon substrate can be sandwiched between two glass covers. The use of a transparent cover results in a window which facilitates dynamic viewing of the channel contents, and allows optical probing of the mesoscale flow system either visually or by machine. Other fabrication approaches may be used. In one embodiment, electron micrographs of biological structures such as circulatory networks may be used as masks for fabricating mesoscale flow systems on the substrate. Mesoscale flow systems may be fabricated in a range of sizes and conformations. The flow system may comprise a nonbranching channel, or alternatively, in a preferred embodiment, the flow system may comprise a fractal region including bifurcations leading to plural secondary channels. In the devices, flow restriction in the mesoscale flow system serves as a positive indicator of the presence of an analyte.

The capacity of the devices is very small and therefore the amount of sample fluid required for an analysis is low. For example, in a 1 cm×1 cm silicon substrate, having on its surface an array of 500 grooves which are 10 microns wide×10 microns deep×1 cm ($10^4$ microns) long, the volume of each groove is $10^{-3}$ μL and the total volume of the 500 grooves is 0.5 μL. The low volume of the mesoscale flow systems allows assays to be performed on very small amounts of a liquid sample (<10 μL). The volume of the flow system typically will be <5 μL, and the volume of individual channels, chambers, or other functional elements are often less than 1 μl, e.g., in the nanoliter or picoliter range. The mesoscale flow systems of the devices may be microfabricated with microliter volumes, or alternatively nanoliter volumes or less, which advantageously limits the amount of sample and/or reagent fluids required for the assay.

An important consequence and advantage of employing flow channels having mesoscale dimensions is that alterations in the flow properties of macromolecules, particles, and cells entrained or dissolved in aqueous liquids within the channels is easily influenced by stenosis, i. e., narrowing of the flow channels, and easily detected. The provision of the fractal region serves to simplify alteration in flow. Thus, for example, a sample suspected to be contaminated with bacteria can be cultured in the device and the presence of a multiplicity of the organism can be detected by determining whether fluid can be forced through the system at a given pressure. Where no bacteria is present, fluid would flow easily; a large number of cells would serve to partially or totally occlude the fractal region. As another example, accretion of macromolecules onto specific binding proteins immobilized on the walls of the flow channel is sufficient to inhibit liquid flow through the channel provided its dimensions are small enough. In still another example, the presence of a target polynucleotide in a polynucleotide sample may be indicated by flowing the contents of a chamber after a suitable number of PCR cycles through a fractal region, as the viscosity of a solution laden with a large amount of polynucleotides will be larger than a solution of nucleotides.

Figure 1:
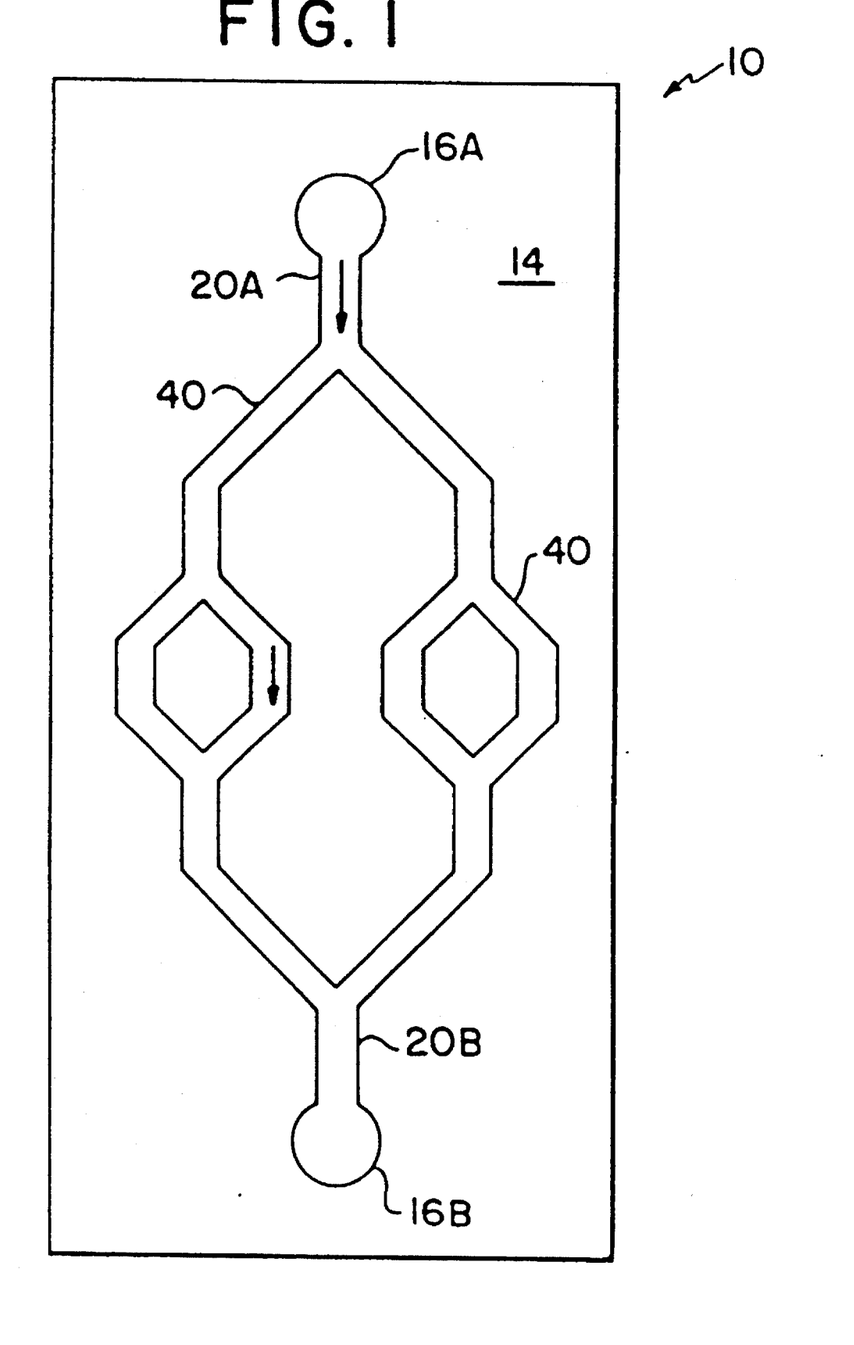
FIG. 1 is a magnified plan view of device 10 according to the invention that comprises substrate 14 microfabricated with ports 16, mesoscale flow channel 20, and a fractally bifurcating system of flow channels 40.
Figure 2:
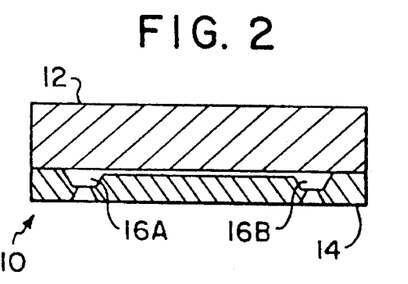
FIG. 2 is a longitudinal cross sectional view of the device shown in FIG. 1.
Figure 3:
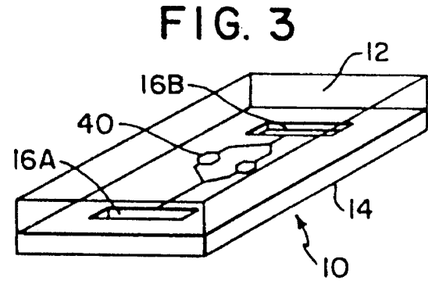
FIG. 3 is a perspective view of the device of FIG. 1.

In one embodiment, illustrated schematically in FIGS. 1, 2 and 3, the device 10 may include a silicon substrate 14 microfabricated with ports 16, primary sample flow channel 20A, and a fractal system of flow channels 40. The ports may be microfabricated with mesoscale or larger dimensions. The fractal region 40 in this case comprises equal numbers of bifurcations and junctions, disposed serially along the direction of flow through the fractal region, leading to a third flow channel 20B. The substrate 14 is covered with a clear glass or plastic window 12 to close the channels. In operation, a fluid sample enters the device through inlet port 16A and flow channel 20A, and then flows through the fractal region 40 to flow channel 20B and port 16B. The fractal region 40 is very sensitive to the flow properties of a sample. Restriction or blockage of flow of a sample through the fractal region 40 can serve as an indicator of the presence of an analyte in the sample and may be detected, e.g., optically through the window 12.

Figure 5:
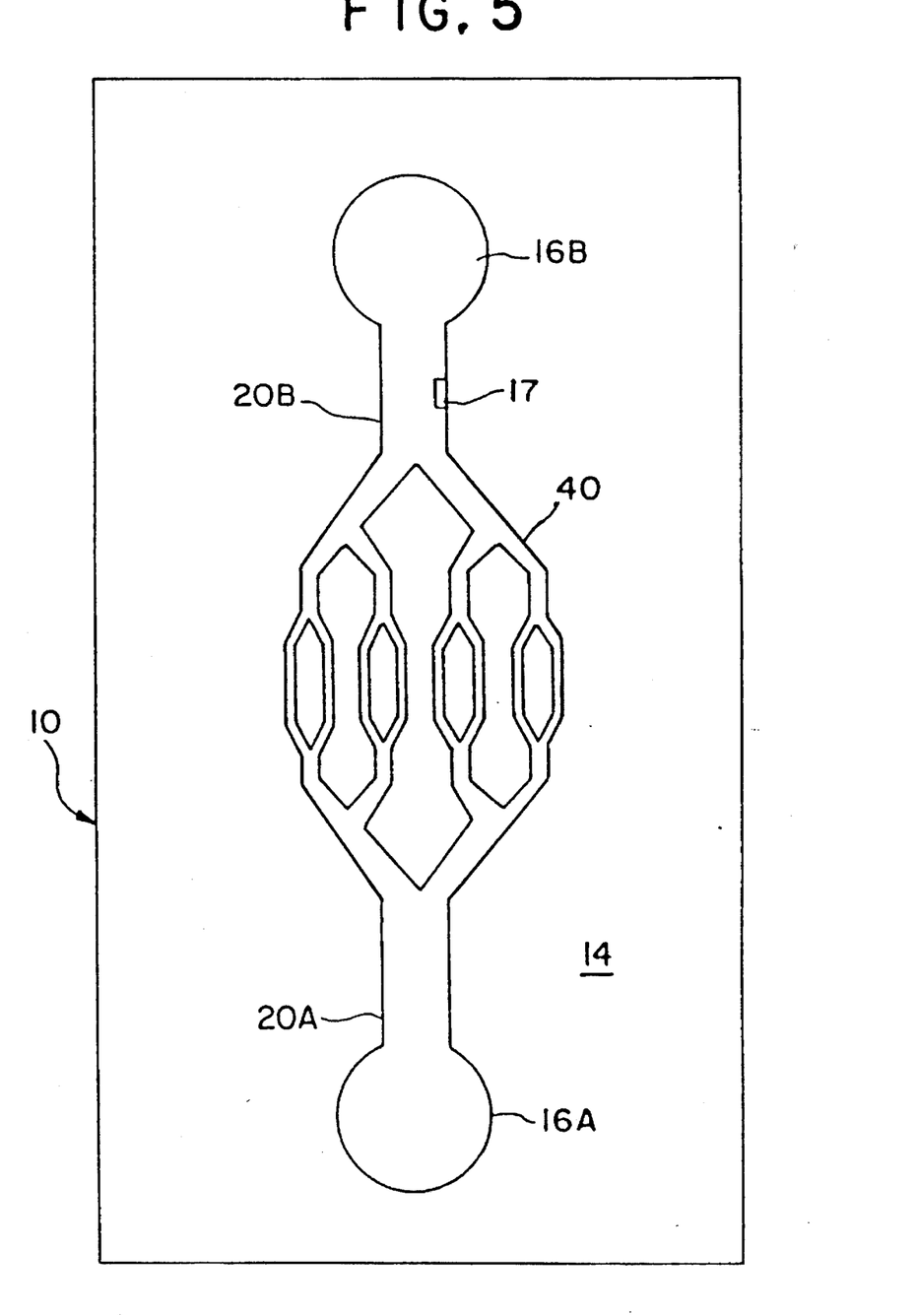
FIG. 5 is a schematic plan view of a substrate 14 microfabricated with a fractally bifurcating system of flow channels 40 symmetrically disposed on the substrate, and tapering to a narrower diameter towards the center of the fractal system.

In another embodiment, the fractal system 40 may be fabricated on a silicon substrate with reduced dimensions at each bifurcation, providing sequentially narrower flow channels, as illustrated schematically in FIG. 5. FIG. 5 shows device 10, which comprises substrate 14 microfabricated with fractal flow channels 40, which have a reduced cross-sectional area relative to the primary flow channel 20A and the third flow channel 20B. In operation, a sample fluid enters the device 10 through inlet port 16A and channel 20A, and then flows through the fractal region 40 to flow channel 20B and port 16B. Fluid flow through this fractal region 40 is very sensitive to changes in fluid viscosity and to the development of flow restriction caused, for example, by the proliferation of cells, or the agglomeration of cells, particles, or macromolecular complexes that may be present in a sample. The fractal system may be microfabricated with a complex series of bifurcations, as illustrated schematically in FIG. 11, to enhance sensitivity to flow restriction. Device 10 in FIG. 11 includes a pair of fractally bifurcating flow channels 40A and 40B. The fractal flow channel 40A is constructed with sequentially narrower flow channels towards the center of the fractal, thereby enhancing sensitivity to flow restriction.

Figure 4:
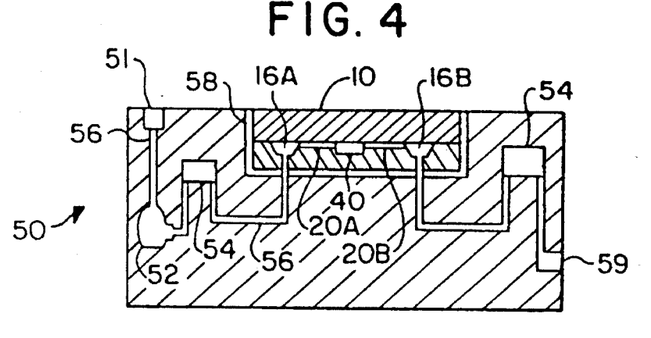
FIG. 4 is a schematic cross sectional view of an analytical device 10 nested within an appliance 50, which is used to support the device 10 and to regulate and detect the pressure of sample fluids in device 10.

The analytical devices containing the mesoscale flow system can be used in combination with an appliance for delivering and receiving fluids to and from the devices, such as appliance 50 shown schematically in FIG. 4, which incorporates a nesting site 58 for holding the device 10, and for registering ports, e.g., ports 16 on the device 10, with a flow line 56 in the appliance. After a fluid sample suspected to contain a particular analyte is applied to the inlet port 51 of the appliance, pump 52 is actuated to force the sample into port 16A of device 10, flow channel 20A, and the fractal region 40. Alternatively, the sample may be injected into the device, or may enter the flow system simply by capillary action. In one embodiment, the flow systems of the devices may be filled to a hydraulically full volume, and the appliance may be utilized to direct the flow of fluid in the mesoscale flow system by means, e.g., of valves located in the device or the appliance. Fluid sample may be discharged from the device through port 59.

Figure 12:
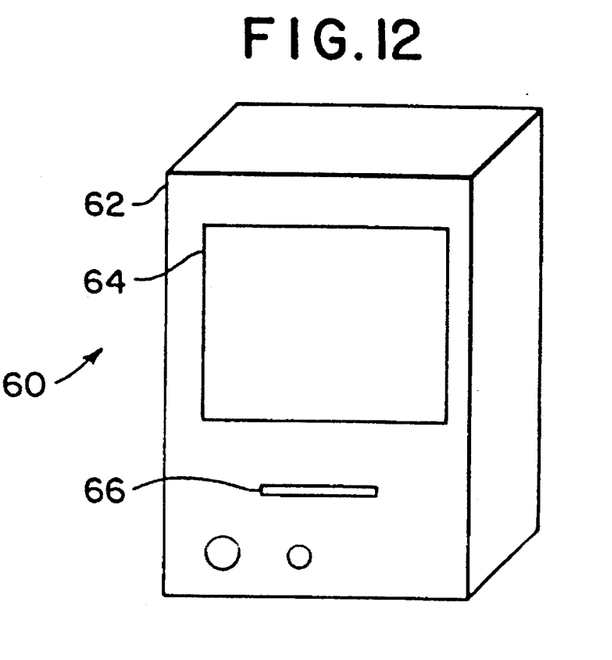
FIG. 12 is a schematic perspective view of an apparatus 60 used in combination with device 10 for viewing the contents of device 10.
Figure 13:
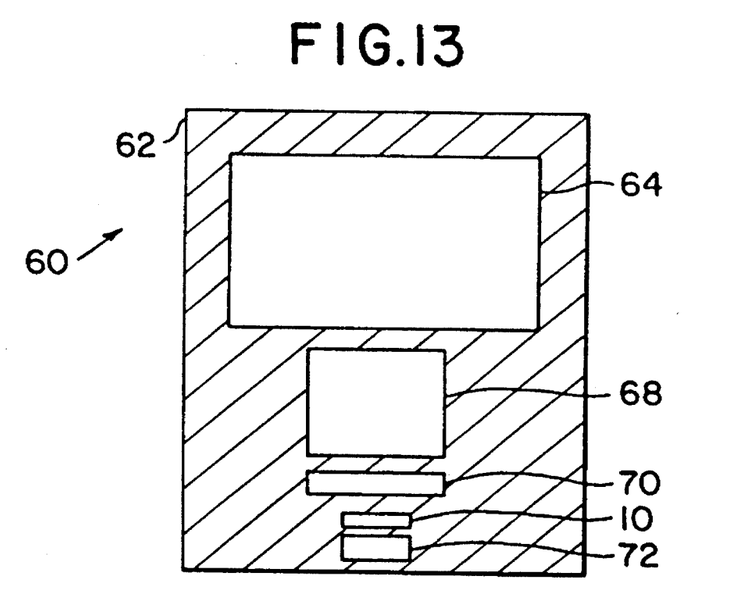
FIG. 13 is a schematic cross sectional view of the apparatus 60 of FIG. 12.

The analytical devices also may be utilized in combination with an appliance for viewing the contents of the mesoscale channels in the devices. The appliance in one embodiment may comprise a microscope for viewing the contents of the mesoscale channels in the devices. In another embodiment, a camera may be included in the appliance, as illustrated in the appliance 60 shown schematically in FIGS. 12 and 13. The appliance 60 is provided with a housing 62, a viewing screen 64 and a slot 66 for inserting a chip into the appliance. As shown in cross section in FIG. 13, the appliance 60 also includes a video camera 68, an optical system 70, and a tilt mechanism 72 for holding device 10, and allowing the placement and angle of device 10 to be adjusted manually. The optical system 70 may include a lens system for magnifying the channel contents, as well as a light source. The video camera 68 and screen 64 allow analyte induced change in sample fluid properties, such as flow properties or color, to be monitored visually, and optionally recorded using the appliance.

Changes in sample flow properties in the flow system, induced by the presence of an analyte in the sample, can be detected by any of a number of methods including monitoring the pressure or electrical conductivity of sample fluids in selected regions of the flow system in the device as disclosed herein. Analyte induced changes in flow properties also may be detected by optical detection through a transparent cover or a translucent section of the substrate itself, either visually or by machine. Devices such as valves, mesoscale pressure sensors, and other mechanical sensors can be fabricated directly on the silicon substrate and can be mass-produced according to well established technologies. Angell et al., *Scientific American*, 248:44–55 (1983). Pressure sensors and other detection means also may be provided in an appliance utilized in combination with the device.

In one embodiment, analyte induced flow restriction can be detected by monitoring the pressure of sample fluids entering and exiting the mesoscale flow system. FIG. 4 shows schematically, as an example, device 10, which is nested within appliance 50, which includes two pressure detectors 54 for detecting flow pressure of fluids entering and exiting device 10 through ports 16. Alternatively, a mesoscale pressure sensor may be fabricated directly on the silicon substrate and connected via electrical contacts to the appliance. Angell et al., *Scientific American*, 248:44–55 (1983). Analyte induced changes in flow properties in the flow system, such as flow restriction, thus may be detected as a pressure change indicative of a positive result. Other detectors may be utilized, such as conventional flow detectors. The movement of magnetic beads entrained in the fluid can be detected easily as an indication of flow restriction.

In another embodiment, electrical conductors may be fabricated in the substrate of the devices to enable transmission of signals indicative of alterations in fluid flow properties, induced by the presence of the analyte, and sensed in different regions of the flow system. Electrical conductors in the substrate may be mated through contacts to the electrical conductors in an appliance, used in combination with the device. The electrical conductors in the device carry signals from pressure or electrical conductivity sensors enabling the detection of the conductivity or pressure of fluid in the flow systems.

For example, in the device 10, illustrated schematically in FIG. 5, analyte induced clogging of the fractal region 40, which blocks flow from inlet port 16A to outlet port 16B, may be detected by a conventional conductivity probe 17 whose output is indicative of the presence or absence of aqueous fluid in the outflow channel. The conductivity or other probe could also be fabricated within the fractal region 40. The substrate may be microfabricated with a control region such that output from the sample flow region and the control region may be detected and compared, thereby enhancing the accuracy of the assay.

In another embodiment, the flow properties between sample fluid entering and exiting the flow system can be detected and compared in order to detect analyte induced changes in flow properties of a sample. In one embodiment, the conductivity may be measured in the device 10 shown schematically in FIGS. 7 and 8. Device 10 includes the silicon substrate 14 on which are microfabricated inlet ports 16 and flow channel 20. The substrate is covered by a translucent window 12.

Figure 7:
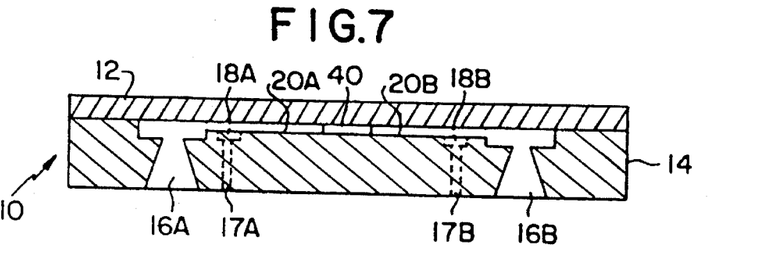
FIG. 7 is a schematic longitudinal cross-sectional view of a device according to the invention which includes electrical conductors 17 and 18 for measuring conductivity of fluids in the device.
Figure 8:
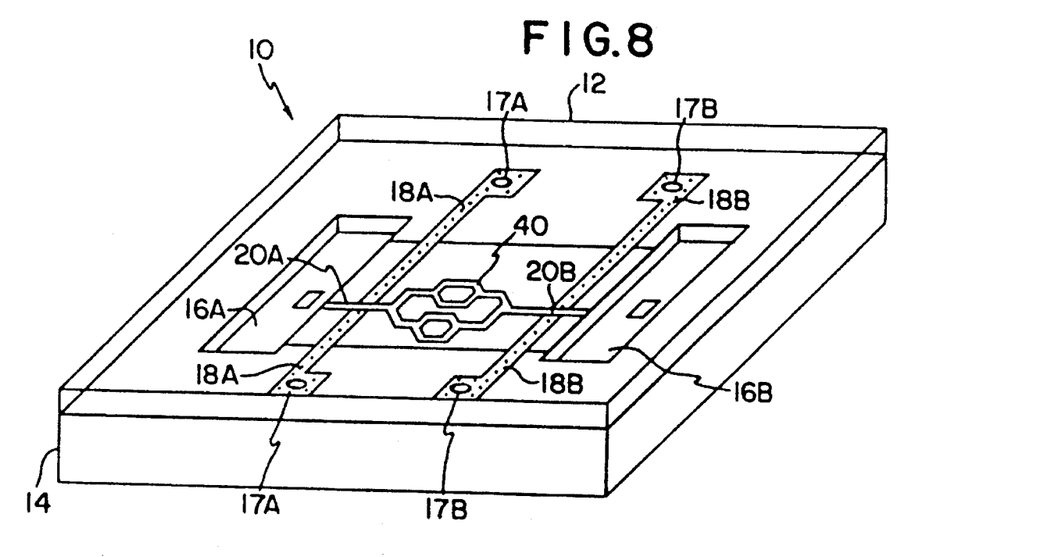
FIG. 8 is a perspective view of the device shown in FIG. 7.

In operation, a sample fluid enters device 10 through port 16A and sample channel 20A, and then flows through the fractal region 40 to channel 20B and port 16B. Device 10 is microfabricated with electrical conductor 18A in electrical contact with fluid channel 20A, for detecting the conductivity of fluid centering the fractal region region 40. The device also includes electrical conductor 18B, in electrical contact with flow channel 20B, for detecting the conductivity of fluid exiting the fractal region 40. The conductors 18 are connected to contacts 17 which extend through to the bottom of the substrate. The contacts 17 can be fabricated by known techniques, e.g., by thermal gradient zone melting. (See Zemel et al., in: *Fundamentals and Applications of Chemical Sensors*, D. Schuetzle and R. Hammerle, Eds., ACS Symposium Series 309, Washington, D.C., 1986, p. 2.) Device 10 may be nested in an appliance such as appliance 50, shown in FIG. 4, capable of detecting conductivity changes through the contacts 17. Changes in conductivity can be correlated with changes in fluid properties, such as fluid pressure, induced by the presence of an analyte, in the fluid sample. Blockage in the fractal will prevent liquid from reaching channel 20B, and the conductivity across the gap in conductor 18B will be low.

Analyte induced changes in flow properties of a sample in the flow systems, such as flow restriction, also may be detected optically, e.g., with a microscope, through a transparent cover over the flow system, or through a transparent region of the substrate itself. The appliance may include sensing equipment, such as a spectrophotometer, to assist in the optical detection of changes in flow properties due to the presence of the analyte.

In one embodiment, the mesoscale flow system, e.g., the fractal region, may comprise a binding moiety, capable of binding the analyte, thereby to enhance flow restriction. Optionally, the binding moiety may be immobilized on the surface of the flow channels, or on a solid phase reactant such as a bead. The binding moiety, may comprise, e.g., an antigen binding protein, a DNA probe, or one of a ligand/receptor pair. The binding moiety may also comprise a crosslinker, such as a chemical reagent or a protein, capable of crosslinking of a specific cell subpopulation.

The binding moiety may be immobilized on the surface of the mesoscale flow channels by, e.g., physical absorption onto the channel surfaces, or by chemical activation of the surface and subsequent attachment of biomolecules to the activated surface. Techniques available in the art may be utilized for the chemical activation of silaceous channel surfaces, and for the subsequent attachment of a binding moiety to the surfaces. (See, e.g., Haller in: *Solid Phase Biochemistry*, W. H. Scouten, Ed., John Wiley, New York, pp 535–597 (1983); and Mandenius et al., *Anal. Biochem.*, 137:106–114 (1984), and *Anal. Biochem.*, 170:68–72 (1988)). The binding moiety may be provided within the mesoscale flow system as disclosed in the copending related application, U.S. Ser. No. 07/877,702 filed May 1, 1992, Mesoscale Detection Structures, the disclosure of which is incorporated herein by reference. The detection of a cellular or chemical analyte can be implemented by selecting the appropriate binding moiety. Flow restriction may be enhanced by the binding of the analyte to the binding moiety, immobilized on the surface of the mesoscale flow system, i.e., by the build-up of a macromolecular surface layer on the surface of the flow system.

Figure 6:
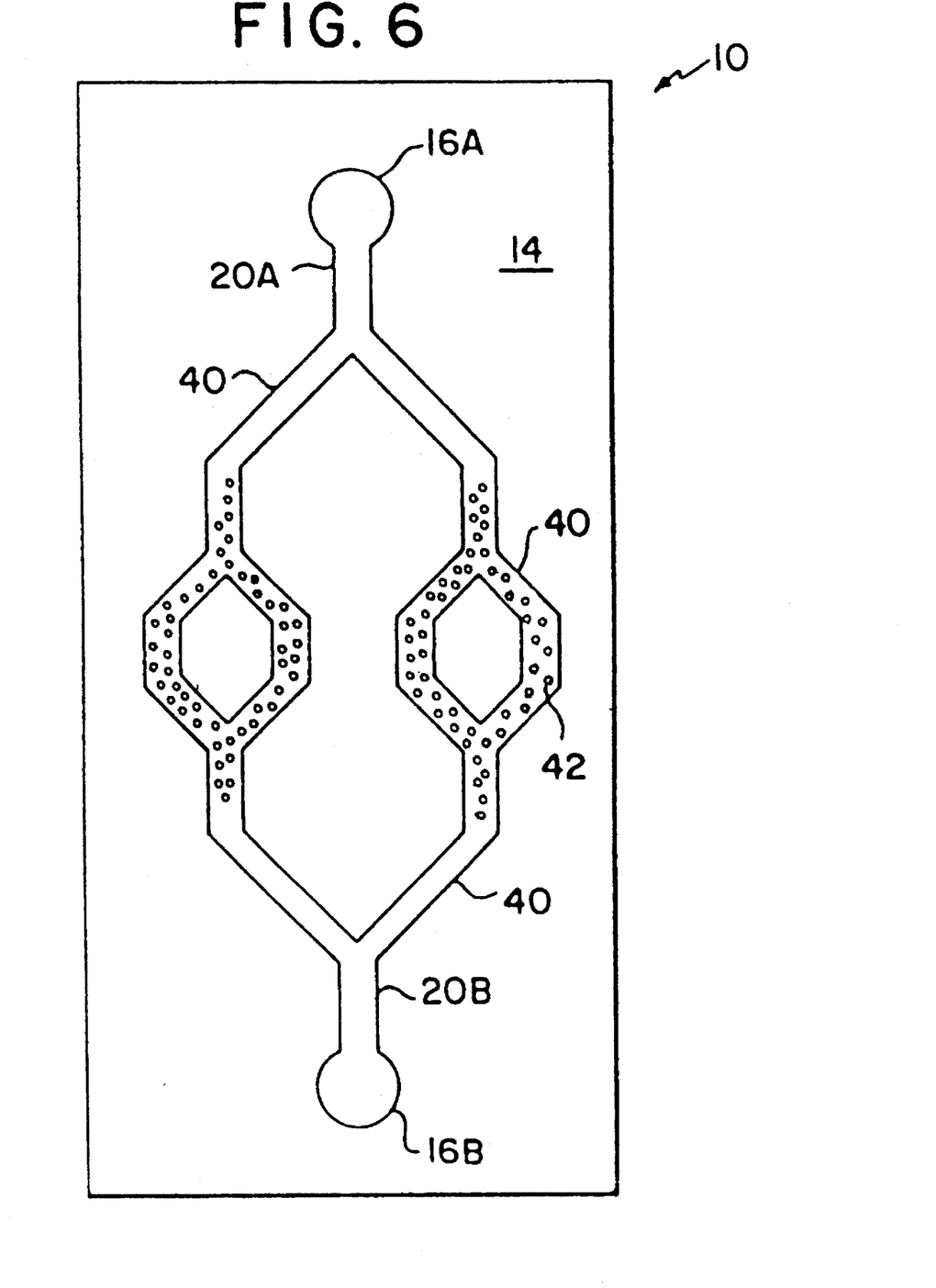
FIG. 6 is a schematic plan view of device 10 that includes substrate 14 microfabricated with entry ports 16, mesoscale flow channel 20, and a fractally bifurcating system of flow channels 40, provided with beads 42 to enhance flow restriction and agglomeration in the fractal.

In one embodiment, the binding moiety may comprise a particle capable of inducing detectable agglomeration of an analyte in the mesoscale flow system. As illustrated in device 10, shown schematically in FIG. 6, particles 42 coated with binding protein specific for a given analyte may be provided in the fractal region 40 to promote analyte-induced agglomeration of fluid in the fractal region. For example, a binding moiety such as an antibody may be immobilized on an inert bead, and may be utilized to induce agglomeration. Agglomeration in the fractal region may be detected optically through a window, e.g., disposed over the fractal region. Agglomeration may also be detected by, e.g., detecting pressure or conductivity changes of the sample fluid as noted below.

In order to enhance the accuracy of an assay, the substrate may be fabricated to include a control region in the flow system, e.g., a region which is identical in geometry to the test region, but does not include binding moieties. Sample directed to both the detection and control regions exhibit different flow properties which may be detected and compared.

Figure 11:
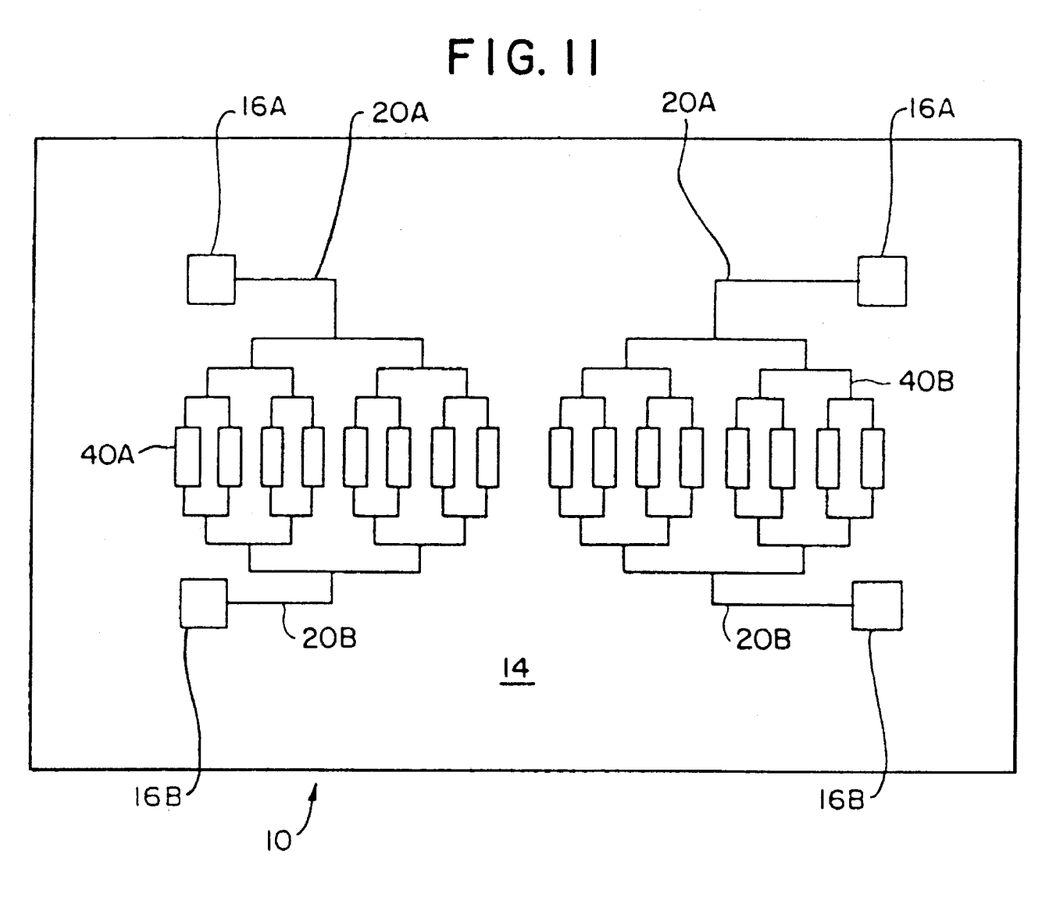
FIG. 11 is a schematic plan view of device 10 according to the invention that includes substrate 14 microfabricated with ports 16, mesoscale flow channels 20, and a pair of fractal flow channels 40.

In one embodiment, the devices provide a mesoscale fractal flow system, which readily allows the growth of organisms in a culture to be monitored on the basis of flow restriction, due to changes in fluid viscosity. The fractal region may include an extensive series of equal numbers of bifurcations and junctions disposed serially along the direction of flow of sample through the region, as schematically illustrated in FIG. 11. Flow restriction may be detected, e.g., optically, after a short incubation. The presence and growth of an organism in a sample will influence the flow characteristics within the fractal. One or more sensors, such as pressure or conductivity sensors, may be utilized to detect pressure changes due to changes in fluid properties caused by the presence of an organism in the fractal region.

In another embodiment, the migration of sperm in the mesoscale flow systems of the devices, e.g., in a fractal region, can serve as an indication of sperm motility. The substrate may be disposed, e.g., in an appliance, at an angle with respect to a horizontal plane, to provide an incline for the travel of a sperm sample, to further enhance the detection of the motility. Reagents capable of binding to a sperm may be provided in the flow system. The devices may be utilized to assess, e.g., a spermicidal agent, the binding properties of a sperm sample, or to conduct sperm counts.

The devices may be used to implement a variety of automated, sensitive and rapid analyses based on flow restriction including analyses of cells or macromolecules, or for monitoring cell culture growth. The devices may be fabricated with two or more mesoscale flow systems which comprise, e.g., two or more different fractal regions, containing, e.g., binding moieties for different analytes, allowing two or more assays to be conducted simultaneously. At the conclusion of the assay the devices typically are discarded. The use of disposable devices eliminates contamination among samples. The sample at all times can remain entombed, and the low volume simplifies waste disposal.

The invention will be understood further from the following nonlimiting examples.

EXAMPLE 1

Sperm motility is tested in the chip 10 shown schematically in FIG. 5. A sample of semen (<2 μL) is placed on a glass microscope slide, and the chip 10 is placed on top of the semen sample such that the port 16A is positioned on the semen sample. The progress of individual spermatozoa into port 16A, through channel 20A and fractal region 40 is monitored using a microscope. The experimental results may be compared with results previously established for a healthy sperm sample to provide a test of sperm motility.

EXAMPLE 2

The growth of an organism is monitored in the device shown schematically in FIG. 5. The fractal pattern of mesoscale flow paths 40 in the substrate 14 are filled via inlet port 16A with 2 μL of a mixture of growth medium which has been inoculated with a sample of a test specimen. The device is sealed and incubated for 60 minutes at 37° C. Growth is detected by visual inspection using a microscope or by determining the flow properties of the channel system, e.g., via the electrical conductivity probe 17. The absence of flow indicates growth and consequent blockage of the fractal system.

EXAMPLE 3

Figure 9:
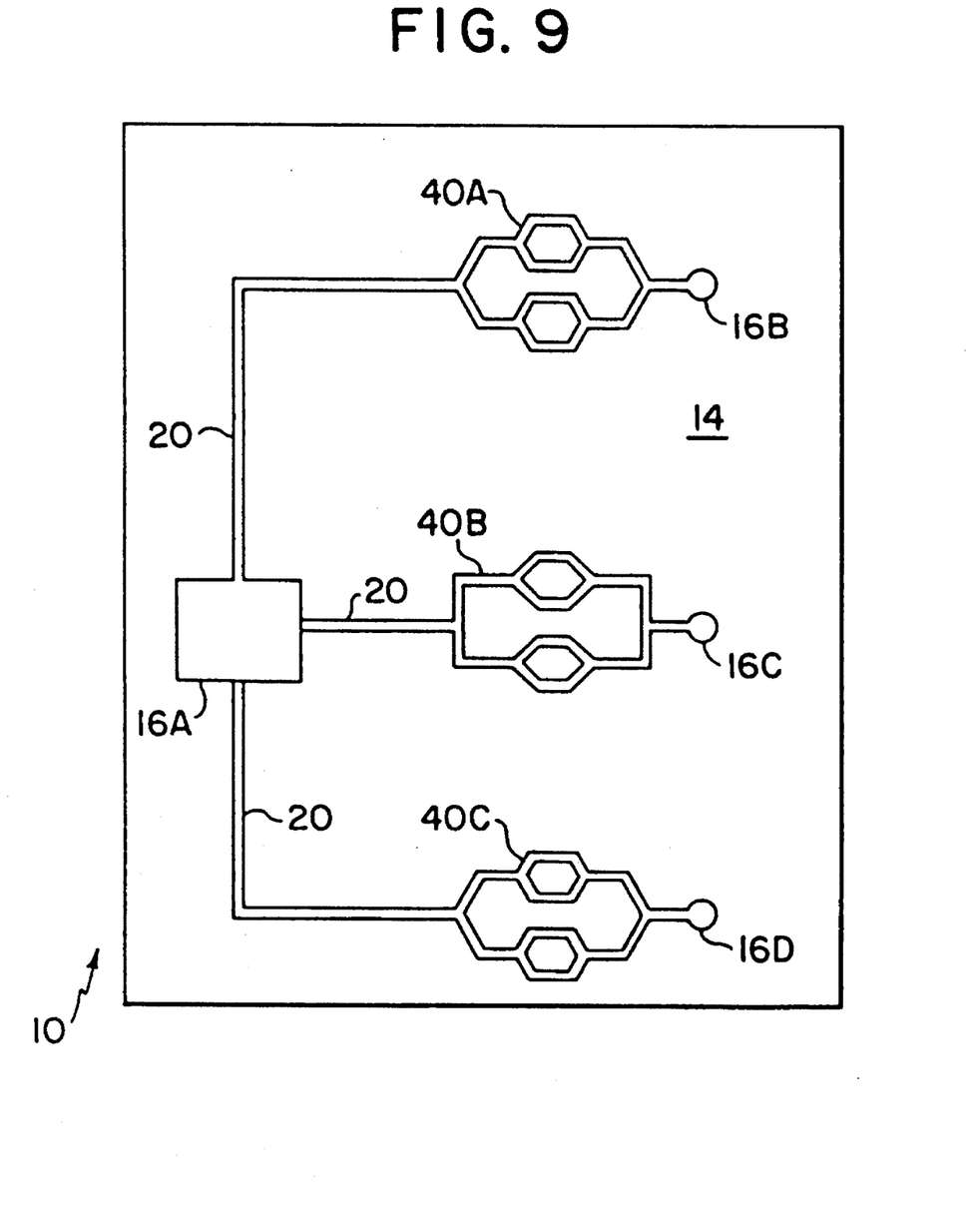
FIG. 9 is a schematic plan view of a multitest apparatus constructed in accordance with the invention.

Sperm functions are tested on the microfabricated solid substrate 14 shown in FIG. 9. A sperm sample is added to the inlet port 16A and then flows through the mesoscale flow channel 20 to the detection chambers 40A, 40B and 40C. Fractal detection chamber 40A provides a test for leucocytes and comprises immobilized antibody to common leukocyte antigen. Fractal detection chamber 40B provides a test for sperm antibodies and contains immobilized antibody to human IgG, IgA or IgM. Fractal detection chamber 40C provides a test for acrosome reaction and contains fluorescein labeled lectin. Flow restriction due to agglutination in the chambers may be detected, e.g., by optical detection through a glass cover disposed over the substrate. After the assay is complete, the device is discarded.

EXAMPLE 4

Figure 10:
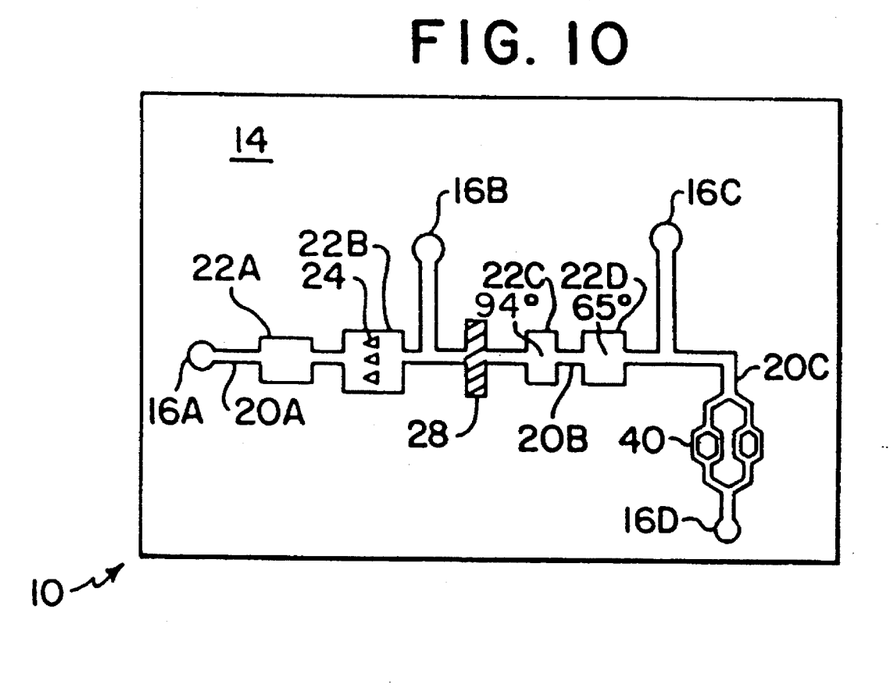
FIG. 10 is a schematic plan view of an analytical device fabricated with a series of mesoscale chambers suitable for implementing a variety of functions including cell sorting, cell lysing, PCR analysis, and detection of PCR products in the fractal region 40.

FIG. 10 depicts schematically a device 10 including substrate 14 used to detect the presence of a target nucleic acid within a subpopulation of cells in a mixture in a biological fluid sample. Microfabricated on device 10 is a mesoscale flow path 20 which includes a cell separation chamber 22A, a cell lysis chamber 22B, a filter region 28, a polymerase chain reaction (PCR) chamber comprising sections 22C and 22D, and a fractal detection region 40. The mesoscale flow system 20 is also provided with fluid entry/ exit ports 16A, 16B, 16C and 16D. The device is used in combination with an appliance, such as appliance 50, shown in FIG. 4. The appliance is provided with fluid paths mated to ports 16 in the device, and valves allowing the ports 16 to be mechanically closed and opened. The appliance also includes pump 52 for regulating the flow of sample fluid through the device. The appliance further includes means for heating the PCR reaction chamber sections 22C and 22D in the device.

Initially, valves in the appliance are used to close ports 16C and 16D, while ports 16A and 16B are open. A sample containing a mixture of cells is directed to the sample inlet port 16A by the pump 52 in the appliance, and flows through the mesoscale flow path 20 to separation chamber 22A. Chamber 22A contains binding moieties immobilized on the wall of the chamber which selectively bind to a surface molecule on a desired type of cell in the sample. Remaining cellular components exit the substrate via port 16B. After binding of the desired cell population in chamber 22A, flow with buffer is continued, to wash and assure isolation of the cell population. Next port 16B is closed and 16C is opened. Flow is then increased sufficiently to dislodge the immobilized cells. Flow is continued, forcing cells through membrane piercing protrusions 24 in chamber 22B, which tear open the cells releasing intracellular material.

Sample flow continues past filter 28, which filters off large cellular membrane components and other debris, to mesoscale PCR chamber section 22C, which is connected to PCR chamber section 22D by flow channel 20B. Taq polymerase, primers and other reagents required for the PCR assay next are added to section 22D through port 16C from a mated port and flow path in the appliance, permitting mixing of the intracellular soluble components from the separated subpopulation of cells and the PCR reagents. With port 16A closed, a pump in the appliance connected via port 16B is used to cycle the PCR sample and reagents through flow channel 20B between sections 22C and 22D, set at 94° C. and 65° C. respectively, to implement plural polynucleotide melting and polymerization cycles, allowing the amplification of product polynucleotide. The mesoscale PCR analysis is performed in accordance with methods disclosed in the related copending application U.S. Ser. No. 07/877,662, Mesoscale Polynucleotide Amplification Analysis, the disclosure of which is incorporated herein by reference.

The valves in the appliance next are used to close port 16C and to open port 16D. The pump in the appliance connected to port 16B is then used to direct the amplified polynucleotide isolated from the cell population to the fractal detection region 40. Flow restriction in the fractal region 40, caused by the presence of amplified polynucleotide product, serves as a positive indicator of the presence of the target DNA or RNA in the cells, and is detected optically through a glass cover disposed over the detection region.

EXAMPLE 5

Experiments were performed in mesoscale flow channels testing the sperm motility of human semen samples. In a sperm motility test, microchannels (60, 80 μm wide, 20 μm deep, and 10 mm long) in a glass-silicon chip were filled with Human Tubal Fluid (HTF) medium (Irvine Scientific, Santa Ana, Calif.) containing 0.5% BSA (HTF-BSA). A sample of semen (<2 μL) was placed on a glass microscope slide and the chip placed on top of the semen sample such that the entrance to the channel was positioned on the semen sample. The progress of individual spermatozoa into the channel and along its length to the exit hole was monitored using a microscope, and recorded using a TV camera and video recorder. Sperm were observed traversing the entire length of the channel and could be seen accumulating in the exit hole. Migration of sperm was also demonstrated in channels of the following depths—40, 100, and 120 μm.

Sperm motility in fractal channels was also examined. The above experiment was repeated using a fractal channel (40 μm wide, 20 μm deep) filled with HTF-BSA medium. Sperm were observed migrating through the tortuous fractal pathway (a total of 9 right angle turns, e.g., the device of FIG. 11) from the entry to the center of the channel. The experiment was repeated using a fractal channel which was 20 μm deep, but which was reduced in width at each bifurcation (40, 30, 25, 20, and 10 μm) and then increased in width (20, 25, 30, 40 μm). Again sperm migrated to the center of the fractal channel.

The bi-directional motility of a sperm sample was also examined. A channel (60 and 80 μm wide, 20 μm deep) and fractal channels were filled with HTF-BSA medium and semen introduced simultaneously via the holes at each end of the channel. Sperm were observed migrating towards the center of the channel (or fractal channel) and eventually passing as they migrated towards the hole at the opposite end of the channel.

An inclined channel experiment was also performed on a sperm sample. A channel (60 μm wide, 20 μm deep) was filled with HTF-BSA medium and a sample of sperm applied to the inlet hole. The inlet and outlet holes were sealed with adhesive tape. The chip was inclined at 45° for different periods of time and then the progression of the sperm up the channel determined visually. Sperm were found to migrate efficiently up the inclined channel and could be seen in the exit hole at the top of the channel.

EXAMPLE 6

An experiment testing different spermicides using a mesoscale flow system was conducted. A chip comprising two chambers (5.2 mm long, 750 μm wide, 1.5 mm deep) each linked at each end to an entry hole by a channel (3.25 mm long, 100 μm wide, 20 μm deep) was used for the simultaneous testing of the spermicidal activity of nonoxynol-9 and C13-G (Biosyn, Inc., Pa.). The four channels were filled with HTF-BSA solution (channel #1, control), 0.005% (channel #2), 0.0125% (channel #3), and 0.05% (channel #4) nonoxynol-9 (or C13-G), respectively. A sample of semen was placed in each chamber and the progress of sperm into the adjoining channels monitored using the microscope. The number of sperm observed in the channels was in the following order of decreasing sperm count: channel #1>#2>#3>#4. Most sperm were seen in the control channel, and none were seen in channel #4 which contained nonoxynol-9 or C13G at the optimum concentration for spermicidal action.

EXAMPLE 7

A morphological examination of motile sperm was conducted in a mesoscale flow system. A chip comprising two chambers (5.2 mm long, 750 μm wide, 1.5 mm deep) each linked at each end to an entry hole by a channel (3.25 mm long, 100 μm wide, 20 μm deep) was used. The channels were filled with HTF-BSA solution and a semen sample applied to the central chamber. The chip was placed in a moist environment for 10 minutes. The surface solution from the holes at each end of the chip was removed and placed on a glass microscope slide (previously washed with ethanol). The slide was dried at 40° C. then stained using Wright Giemsa stain (Curtin Matheson Scientific, Inc., Houston, Tex.). The sperm which had migrated from the cental chamber to the end of the channel and into the hole had a normal morphological appearance.

EXAMPLE 8

The interaction of a sperm sample with cervical mucus in a mesoscale flow sytem was tested in a chip comprising two chambers (5.2 mm long, 750 μm wide, 1.5 mm deep) each linked at each end to an entry hole by a channel (3.25 mm long, 100 μm wide, 20 μm deep). The channels were filled with HTF-BSA solution and a cervical mucus sample (collected at approximately day 14 of the patient's menstrual cycle) placed in each of the central chambers. Sperm did not migrate into the cervical mucus and those that penetrated died, as anticipated because cervical mucus is known to be hostile to sperm at this time during the menstrual cycle. Moghissi et al., *Am. J. Obstet. Gynecol.*, 114:405 (1972).

EXAMPLE 9

A test of the interaction of hyaluronic acid with a sperm sample was conducted to assess the cervical interaction of a sperm sample. The test was conducted in a chip comprising two chambers (5.2 mm long, 750 μm wide, 1.5 mm deep) each linked at each end to an entry hole by mesoscale flow Channels #1, #2, #3 and #4 (3.25 mm long, 100 μm wide, 20 μm deep). Channel #1 was a control channel. Channels were filled with HTF-BSA solution and solutions of hyaluronic acid (Sigma) in HTF-BSA (channels #2, #3, #4, 5 mg/mL, 2.5 mg/mL, and 1.3 mg/mL, respectively). A semen sample was placed in each of the central chambers. Sperm did not migrate into channel #2, containing 5 mg/mL hyaluronic acid, but the extent of migration increased as the concentration of hyaluronic acid decreased in channels #3 and #4.

EXAMPLE 10

An immunobead test for the presence of IgG antibodies in a sperm sample was conducted. Immunobeads (BioRAD, Richmond, Calif.), microbeads coated with an antibody to human IgG, were diluted to 1 mg/mL in HTF-BSA solution (Irvine Scientific, Santa Ana, Calif.). A microchannel (250 μm wide, 20 μm deep, and 10 mm long) in a glass-silicon chip was filled with a sample of the immunobead solution and a semen sample (ca 1.2 μL) was applied to the channel entry. Agglutination of sperm by the immunobeads due to the presence of antibodies in the sperm sample was observed in the channel. As a control, the experiment was performed on a glass microscope slide using larger volumes of the immunobead reagent and semen sample, and this was also positive (agglutination observed).

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. A device for detecting the presence of an analyte in a fluid sample, the device comprising:

a solid substrate microfabricated to define:

a sample inlet port; and a mesoscale flow system comprising:

a primary sample flow channel extending from said inlet port; and a fractal region, in fluid communication with said primary flow channel, comprising bifurcations leading to plural secondary flow channels; and means for detecting a flow property of a fluid sample in said flow system as an indication of the presence of an analyte in the fluid sample.

2. The device of claim 1 wherein said fractal region further comprises junctions in fluid communication with said secondary flow channels leading to a third flow channel in said mesoscale flow system.

3. The device of claim 1 further comprising means for inducing flow of said sample through said mesoscale flow system.

4. The device of claim 2 wherein said fractal region comprises equal numbers of bifurcations and junctions disposed serially along the direction of flow of the sample through said fractal region.

5. The device of claim 4, wherein the fractal region has a reduced cross-sectional area relative to said primary flow channel and said third flow channel.

6. The device of claim 3, wherein said means for detecting comprises means for detecting analyte induced restriction of flow through said flow system.

7. The device of claim 2 wherein said means for detecting comprises means for detecting a parameter in said third flow channel.

8. The device of claim 2, wherein said means for detecting comprises means for detecting and comparing a parameter in said primary sample flow channel with a parameter in said third flow channel.

9. The device of claim 7 or 8 wherein said means for detecting comprises an electrical detection means.

10. The device of claim 7 wherein said parameter is fluid pressure.

11. The device of claim 7 wherein said parameter is fluid conductivity.

12. The device of claim, 1 wherein said means for detecting comprises means for detecting a parameter in said fractal region.

13. The device of claim 12 wherein said detecting means comprises means defining an optical path to said fractal region.

14. The device claim 1 further comprising a binding moiety disposed within said fractal region for binding the analyte of said sample.

15. The device of claim 14 wherein said binding moiety comprises particles which bind with the analyte of said sample to induce particle agglomeration.

16. The device of claim 1 wherein said means for detecting comprises a magnetic detection means.

17. The device of claim 1 wherein said substrate defines a plurality of said flow systems.

18. The device of claim 1 wherein said means for detecting comprises means for detecting the growth of an organism in said flow system.

19. The device of claim 1 wherein the sample is a sperm sample and wherein flow of sperm through the fractal region provides an indication of sperm motility.

20. The device of claim 19, wherein a channel in said substrate is disposed at an angle with respect to a horizontal plane.

21. The device of claim 1 where said solid substrate comprises microfabricated silicon.

22. The device of claim 1, further comprising an appliance for use in combination with said substrate, said appliance comprising:

means for holding said substrate;

fluid input means interfitting with the inlet port on said substrate; and pump means for passing fluid through the flow system of said substrate when said substrate is held in said holding means.

23. The device of claim 1, wherein said means for detecting comprises an appliance for use in combination with said substrate, said appliance comprising:

means for holding said substrate; and optical means for viewing the contents of said mesoscale flow system in said substrate.

24. The device of claim 23, wherein said optical means comprises magnifying optics and a video camera, and wherein said appliance further comprises:

a tilt mechanism for manually adjusting the angle and location of the device; and a video screen for viewing the contents of said flow system.

25. The device of claim 1 wherein said flow system includes a control fractal region permitting comparison of flow of said sample in said fractal region and said control fractal region.

26. A method for detecting the presence or absence of an analyte in a fluid sample, the method comprising the steps of:

(i) providing a device comprising:
a solid substrate microfabricated to define:
a sample inlet port; and
a mesoscale flow system comprising:
a primary sample flow channel extending from said inlet port; and
a fractal region, in fluid communication with said primary flow channel, comprising bifurcations leading to plural secondary flow channels;

(ii) passing a fluid sample suspected to contain an analyte through said mesoscale flow system;

(iii) detecting the restriction or blockage of flow of the fluid sample through said system; and (iv) correlating the detected restriction or blockage of flow, or lack of said detected restriction or blockage of flow, to the presence or absence of an analyte in said sample.

27. The method of claim 26, wherein said flow system comprises a binding moiety, capable of binding said analyte in said sample, to promote said restriction or blockage of flow through said system.

28. The method of claim 27 wherein said binding moiety is disposed on particles which bind with said analyte in said sample to induce particle agglomeration, thereby to promote said restriction or blockage of flow.

29. The method of claim 27 wherein said analyte is a cell population in said sample;

said binding moiety comprises a crosslinker of cells in said population; and said restriction of flow is caused by crosslinker-induced cell aggregation.

30. The method of claim 27 wherein said binding moiety is immobilized within said flow system.

31. The method of claim 30 wherein flow is restricted by the build-up of a macromolecular surface layer on a surface of said flow system.

32. The method of claim 26 wherein said fractal region further comprises junctions in fluid communication with said secondary flow channels leading to a third channel in said flow system, to amplify the effect of occlusion of said flow system or increase in viscosity within said substrate.

33. The method of claim 26 wherein, in step (iii), restriction or blockage is detected electrically.

34. The method of claim 26 wherein, in step (iii), restriction or blockage is detected optically.

35. The method of claim 32 wherein said fractal region further comprises a binding moiety for binding the analyte of said sample.

36. The method of claim 35 wherein said binding moiety contains particles which bind with the analyte of said sample to induce particle agglomeration.

37. The method of claim 26, wherein said substrate, provided in step (i), further comprises a control region in fluid communication with said sample inlet port; and wherein, in step (iii), flow of said sample in said fractal region and said control region is detected and compared.

38. The method of claim 26 wherein the analyte comprises a replicable procaryotic organism; and wherein, in step (iii), the restriction or blockage of flow of said organism through said flow system serves as an indication of the presence of said organism.

39. A method for detecting the presence of an analyte in a fluid sample, the method comprising the steps of:

(i) providing a device comprising:
a solid substrate microfabricated to define:
a sample inlet port; and
a mesoscale flow system comprising:
a primary sample flow channel extending from said inlet port; and
a fractal region, in fluid communication with said primary flow channel, comprising bifurcations leading to plural secondary flow channels;

(ii) passing a fluid sample suspected to contain an analyte through said mesoscale flow system;

(iii) detecting a flow property of the fluid sample in the flow system; and (iv) correlating the detected flow property of the fluid sample to the presence or absence of an analyte in the sample.

40. The method of claim 39 wherein said fractal region further comprises junctions, in fluid communication with the secondary flow channels, leading to a third flow channel.

41. The method of claim 32 or 40 wherein said fractal region comprises equal numbers of bifurcations and junctions disposed serially along the direction of flow of the sample through said fractal region.

42. The device of claim 1, 4 or 25 wherein, within at least a portion of a channel in said flow system, each of the channel width and channel depth is between 0.1 μm and 500 μm.

43. The device of claim 42 wherein the channel width in said portion is between 2.0 and 300 μm.

44. The device of claim 42 wherein the channel depth in said portion is between 0.1 and 100 μm.

45. The method of claim 26, 39 or 40 wherein, within at least a portion of a channel in said flow system, the channel width and channel depth each are between 0.1 μm and 500 μm.

46. The method of claim 45 wherein the channel width in said portion is between 2.0 and 300 μm.

47. The method of claim 45 wherein the channel depth in said portion is between 0.1 and 100 μm.

* * * * *